(12) United States Patent
Murashita et al.

(10) Patent No.: US 7,604,597 B2
(45) Date of Patent: Oct. 20, 2009

(54) ULTRASONIC DIAGNOSTIC APPARATUS

(75) Inventors: Marasu Murashita, Mitaka (JP); Akinori Seta, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 697 days.

(21) Appl. No.: 10/771,816

(22) Filed: Feb. 4, 2004

(65) Prior Publication Data
US 2004/0210138 A1   Oct. 21, 2004

(30) Foreign Application Priority Data
Apr. 21, 2003   (JP)   ............................ 2003-115340

(51) Int. Cl.
*A61B 8/00* (2006.01)

(52) U.S. Cl. .................. 600/443; 600/447; 600/450; 128/916

(58) Field of Classification Search ................. 600/443, 600/425; 382/128
See application file for complete search history.

(56) References Cited

U.S. PATENT DOCUMENTS

| | | | |
|---|---|---|---|
| 5,497,776 A * | 3/1996 | Yamazaki et al. | 600/445 |
| 5,771,895 A * | 6/1998 | Slager | 600/462 |
| 5,825,908 A * | 10/1998 | Pieper et al. | 382/131 |
| 5,891,030 A * | 4/1999 | Johnson et al. | 600/407 |
| 6,148,095 A * | 11/2000 | Prause et al. | 382/131 |
| 6,342,889 B1 | 1/2002 | Callahan | |
| 6,352,509 B1 | 3/2002 | Kawagishi et al. | |
| 6,928,314 B1 * | 8/2005 | Johnson et al. | 600/407 |
| 7,103,202 B2 * | 9/2006 | Bruijns | 382/128 |
| 7,149,333 B2 * | 12/2006 | Pieper et al. | 382/128 |
| 7,149,564 B2 * | 12/2006 | Vining et al. | 600/425 |
| 2001/0024516 A1 | 9/2001 | Yoshioka et al. | |
| 2001/0031920 A1 * | 10/2001 | Kaufman et al. | 600/431 |
| 2003/0208116 A1 * | 11/2003 | Liang et al. | 600/407 |

FOREIGN PATENT DOCUMENTS

| | | |
|---|---|---|
| EP | 0 974 931 | 1/2000 |
| EP | 1 433 422 | 6/2004 |
| JP | 2002-245487 | 8/2002 |

OTHER PUBLICATIONS

Jos R.T.C. Roelandt, "Three-dimensional echocardiography: the future today!", Computers and Graphics, Pergamon Press Ltd. Oxford, GB, vol. 24, No. 5, Oct. 2000, pp. 715-729.

* cited by examiner

*Primary Examiner*—Eric F Winakur
*Assistant Examiner*—Michael T Rozanski
(74) *Attorney, Agent, or Firm*—William L. Androlia; H. Henry Koda (57) ABSTRACT

A specific cavity extractor extracts an isolated group corresponding to a left ventricle from among a plurality of isolated groups to which numbers are attached in a labeling section. A major axis slope calculator section sets, as a left ventricle major axis, a straight line passing through a center of mass calculated in a center-of-mass detector section and a major-axis end point detected in a major-axis end detector section. A cavity cross sectional area calculator section calculates a cross sectional area of four cavities for each of a plurality of cutting planes including the left ventricle major-axis. An optimum cross section setter sets, as a four-cavity cross section, a cutting plane in which the cross sectional area of the four cavities becomes maximum.

10 Claims, 4 Drawing Sheets

ULTRASONIC DIAGNOSTIC APPARATUS

BACKGROUND OF THE INVENTION

1. Field of the Invention

The present invention relates to an ultrasonic diagnostic apparatus and in particular to a three-dimensional ultrasonic diagnostic apparatus having a function to display an arbitrary cross section.

2. Description of the Related Art

Ultrasonic diagnostic apparatuses are known in which ultrasound is transmitted to/from a three-dimensional space including a target tissue to obtain three-dimensional image data and an arbitrary cross section of the target tissue is displayed based on the three-dimensional image data. For example, Japanese Patent Laid-Open Publication No. 2002-245487 discloses an ultrasonic diagnostic apparatus which displays a synthesized image of a three-dimensional image and an image of an arbitrary cross section, and, at the same time, displays a cross sectional image which is an image of the arbitrary cross section viewed from the front. This type of ultrasonic diagnostic apparatus which has a function to display an arbitrary cross section is effective in ultrasonic diagnosis of a heart.

In an ultrasonic diagnosis of a heart, for example, an ultrasonic diagnosis of a left ventricle of a heart, the diagnosing person desires a cross sectional image in which the intracardial portion of the left ventricle enlarged. For this purpose, the diagnosing person suitably moves the cutting plane while viewing a three-dimensional image and/or cross sectional image displayed on the ultrasonic diagnosis apparatus to specify an optimum cross section.

In order to specify an optimum cross section in a three-dimensional space, however, it is necessary to set translational movement of the cross section and/or rotational movement of the cross section with respect to each axis (for example, x axis, y axis, and z axis). In other words, a diagnosing person is required to repeatedly execute setting of translational movement of the cross section and/or rotational movement of the cross section with respect to each axis while viewing the three-dimensional image and/or cross sectional image displayed on the ultrasonic diagnostic apparatus. Because of this, the operation to set an optimum cross section becomes complicated and requires expertise.

SUMMARY OF THE INVENTION

The present invention advantageously provides an ultrasonic diagnostic apparatus in which an optimum cross section can be easily set.

According to one aspect of the present invention, there is provided an ultrasonic diagnostic apparatus for obtaining volume data made of voxel values for voxels forming a three-dimensional space by transmitting and receiving ultrasound to and from the three-dimensional space containing a target tissue and for applying a data process with respect to the volume data, the ultrasonic diagnostic apparatus comprising a basis axis setter for setting a basis axis in the target tissue based on a characteristic of the target tissue; a reference cross section setter for setting, with respect to the target tissue, a plurality of reference cross sections which intersect each other with the basis axis as a reference; a basis cross section selector for selecting a basis cross section from among the plurality of reference cross sections based on a cross sectional characteristic (for example, a brightness of a tissue within a cross section, across sectional area, or a peripheral length of the cross section) of the target tissue in each of the reference cross sections; and a cross sectional image former for forming a cross sectional image of the target tissue, the cross sectional image corresponding to one of cross sections set with the basis cross section as a reference and the basis cross section.

With the above structure, because the basis cross section selector selects a basis cross section and the cross sectional image former forms a cross sectional image at the basis cross section or at a cross section which is set based on the basis cross section, an optimum cross section can be set without a complicated setting operation by the user. The cross section which is set based on the basis cross section is, for example, a cross section which is orthogonal to the basis cross section.

According to another aspect of the present invention, it is preferable that, in the ultrasonic diagnostic apparatus, the basis axis setter sets the basis axis based on two characteristic points of the target tissue. According to another aspect of the present invention, it is preferable that, in the ultrasonic diagnostic apparatus, the basis axis setter sets the basis axis based on a center of mass of the target tissue and one characteristic point of the target tissue other than the center of mass. According to another aspect of the present invention, it is preferable that, in the ultrasonic diagnostic apparatus, the basis axis setter sets the basis axis based on the center of mass of the target tissue and an end, in the target tissue, which is furthest away from the center of mass. According to another aspect of the present invention, it is preferable that, in the ultrasonic diagnostic apparatus, the reference cross section setter sequentially rotates a specific plane containing the basis axis by a predetermined angle with the basis axis as an axis of rotation, to set the planes formed in each rotational angle position as the plurality of reference cross sections. According to another aspect of the present invention, it is preferable that, in the ultrasonic diagnostic apparatus, the basis cross section selector calculates an area of a cross section of the target tissue in each reference cross section and selects, as the basis cross section, a reference cross section having a maximum cross sectional area or a minimum cross sectional area. According to another aspect of the present invention, it is preferable that, in the ultrasonic diagnostic apparatus, the basis cross section selector calculates a peripheral length of the target tissue in each reference cross section and selects, as the basis cross section, a reference cross section in which a longest peripheral length or a shortest peripheral length can be obtained.

According to another aspect of the present invention, there is provided an ultrasonic diagnostic apparatus for obtaining volume data made of voxel values for voxels forming a transmission space by transmitting and receiving ultrasound to or from a heart having four cavities including a left ventricle cavity and for applying a data process to the volume data, the ultrasonic diagnostic apparatus comprising: a major axis setter for setting a left ventricle major axis based on the shape of the left ventricle cavity; a reference cross section setter for setting a plurality of reference cross sections each having a different rotational angle from each other, with the left ventricle major axis as an axis of rotation; a basis cross section selector for selecting a basis cross section from among the plurality of reference cross sections based on a size of a cross section of the four cavities in each of the reference cross sections; and a cross sectional image former for forming a cross sectional image corresponding to at least one of a four-cavity cross section, a two-cavity cross section, and a minor-axis cross section, all of which relate to the heart, based on the basis cross section.

The left ventricle of the heart contains characteristic portions such as an apex section of heart and a mitral valve. The major-axis setter may set the left ventricle major axis using, for example, these characteristic portions. Alternatively, a position of the center of mass of the left ventricle cavity and a position of an inner cavity surface may be used for setting the left ventricle major axis. With the above structure, because the cross sectional image former set at least one of the four-cavity cross section, two-cavity cross section, and the minor-axis cross section based on the basis cross section, it is possible to set the optimum cross section without a complicated cross setting operation of a cross section by the user.

According to another aspect of the present invention, it is preferable that the ultrasonic diagnostic apparatus further comprises a binarization section for separating the voxels into a cavity tissue voxel and a real tissue voxel to create binarized volume data; a cavity group extractor for extracting a plurality of cavity groups each made of a plurality of cavity tissue voxels based on the binarized volume data; and a left ventricle cavity selector for selecting a left ventricle cavity group corresponding to the left ventricle cavity from among the plurality of cavity groups, and that the major axis setter judges the shape of the left ventricle cavity based on the left ventricle cavity group.

According to another aspect of the present invention, it is preferable that, in the ultrasonic diagnostic apparatus, the basis cross section selector calculates a cross sectional area of the four cavities in each of the reference cross sections and selects, as the basis cross section, a reference cross section in which a maximum cross sectional area can be obtained, and the cross sectional image former sets the basis cross section as the four-cavity cross section. According to another aspect of the present invention, it is preferable that, in the ultrasonic diagnostic equipment, the two-cavity cross section is a cross section which is orthogonal to the basis cross section and which contains the left ventricle major axis. According to another aspect of the present invention, it is preferable that, in the ultrasonic diagnostic equipment, the minor-axis cross section is a cross section which is orthogonal to the left ventricle major axis and which contains a center of mass of the left ventricle cavity.

According to another aspect of the present invention, it is preferable that the ultrasonic diagnostic apparatus further comprises a three-dimensional image former for forming a three-dimensional image in which at least one cursor indicating at least one of the positions of the four-cavity cross section, the two-cavity cross section, and the minor-axis cross section is displayed on a stereographical image of the heart obtained based on the volume data.

According to another aspect of the present invention, there is provided an ultrasonic diagnostic apparatus for obtaining, from an ultrasonic probe for transmitting and receiving ultrasound to and from a transmission space containing a heart, volume data made up of voxel values of voxels forming the transmission space, and for applying a data process to the volume data, the ultrasonic diagnostic equipment comprising a major axis setter for setting a left ventricle major axis based on a shape of a left ventricle cavity of the heart; a reference cross section setter for setting a plurality of reference cross sections each having a different rotational angle, with the left ventricle major axis as an axis of rotation; a basis cross section selector for selecting a basis cross section from among the plurality of reference cross sections based on a size of a cross section of the four cavities in each of the reference cross sections; and a cross sectional image data former for forming, based on the basis cross section, image data of a cross sectional image corresponding to at least one of a four-cavity cross section, a two-cavity cross section, and a minor-axis cross section regarding the heart.

According to another aspect of the present invention, it is preferable that the ultrasonic, diagnostic apparatus further comprises a binarization section for separating the voxels into cavity tissue voxels and real tissue voxels to create binarized volume data; a cavity group extractor for extracting, based on the binarized volume data, a plurality of cavity groups each made of a plurality of cavity tissue voxels; and a left ventricle cavity selector for selecting a left ventricle cavity group corresponding to the left ventricle cavity from among the plurality of cavity groups, and that the major axis setter judges a shape of the left ventricle cavity based on the left ventricle cavity group.

According to another aspect of the present invention, it is preferable that, in the ultrasonic diagnostic apparatus, the basis cross section selector calculates a cross sectional area of the four cavities in each of the reference cross sections and selects, as the basis cross section, a reference cross section in which a maximum cross sectional area can be obtained, and the cross sectional image former sets the basis cross section as the four-cavity cross section. According to another aspect of the present invention, it is preferable that, in the ultrasonic diagnostic apparatus, the two-cavity cross section is a cross section which is orthogonal to the basis cross section and contains the left ventricle major axis. According to another aspect of the present invention, it is preferable that, in the ultrasonic diagnostic apparatus, the minor-axis cross section is a cross section which is orthogonal to the left ventricle major axis and which contains a center of mass of the left ventricle cavity. According to another aspect of the present invention, it is preferable that the ultrasonic diagnostic apparatus further comprises a three-dimensional image data former for forming image data of a three-dimensional image in which at least one cursor indicating at least one of the positions of the four-cavity cross section, the two-cavity cross section, and the minor-axis cross section is displayed on a stereographical image of the heart obtained based on the volume data.

DESCRIPTION OF PREFERRED EMBODIMENT

A preferred embodiment of the present invention will now be described referring to the drawings.

Figure 1:
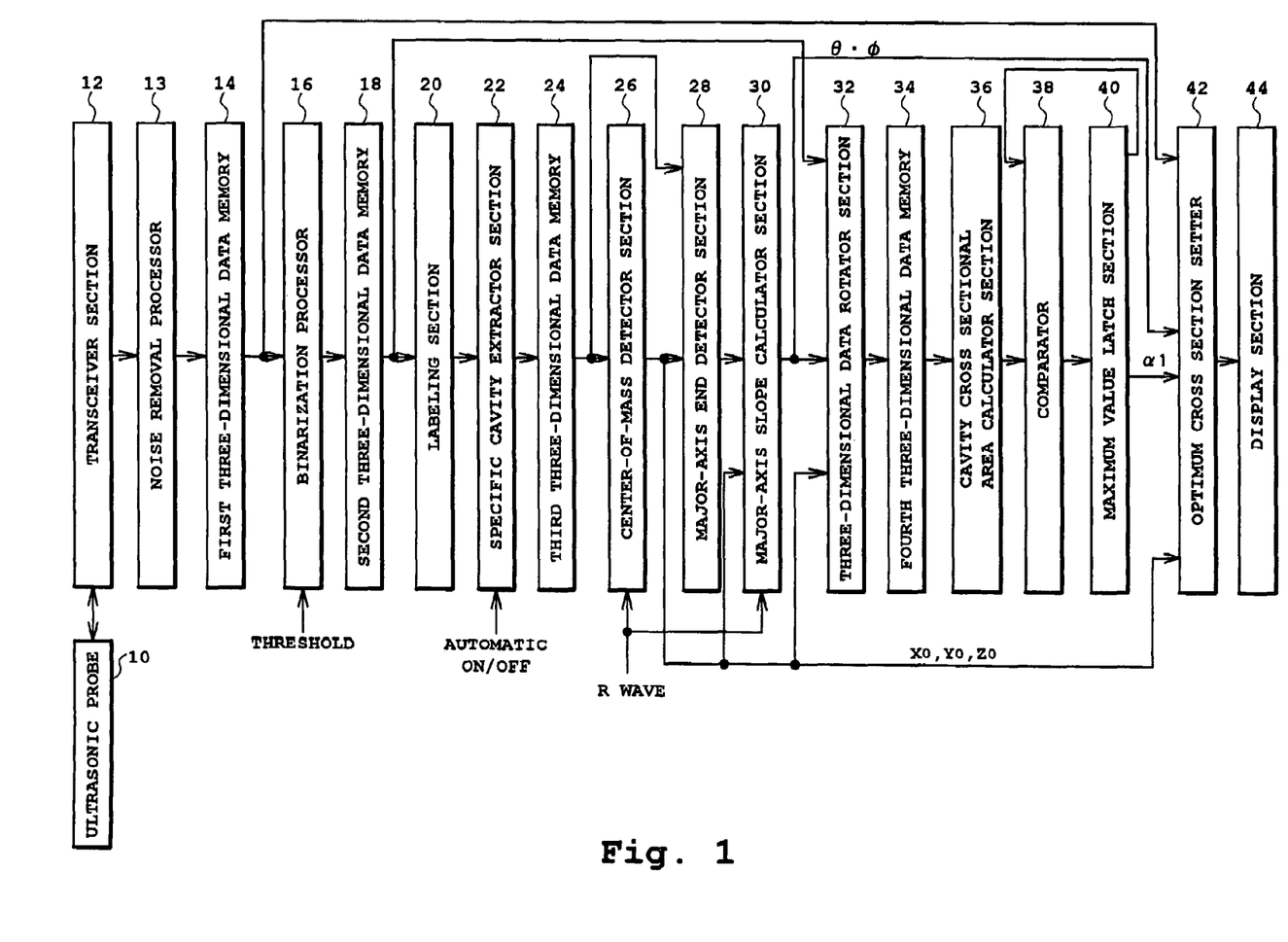
FIG. 1 is a block diagram showing an overall structure of an ultrasonic diagnostic apparatus according to a preferred embodiment of the present invention.

FIG. 1 is a block diagram showing an overall structure of an ultrasonic diagnostic apparatus according to a preferred embodiment of the present invention. FIGS. 2-5 are diagrams illustrating processes applied in each section of the ultrasonic diagnostic apparatus shown on FIG. 1. An operation of the ultrasonic diagnostic apparatus shown on FIG. 1 will be described referring to FIGS. 2-5.

An ultrasonic probe 10 is an ultrasonic probe for obtaining three-dimensional echo data. The ultrasonic probe 10 is used in contact with the skin of a patient or is inserted into a body cavity. The ultrasonic probe 10 transmits or receives ultrasound to or from a three-dimensional space by mechanically scanning a 1-D array oscillator which transmits or receives ultrasound to or from a two-dimensional space by electrical scanning. Alternatively, the ultrasonic probe 10 may transmit or receive ultrasound to or from a three-dimensional space by electrical scanning of a 2-D array oscillator formed by a two-dimensional matrix of oscillators.

A transceiver section 12 controls the ultrasonic probe 10 and transmits or receives ultrasound to or from a three-dimensional space including a heart which is a target tissue. In other words, the transceiver section 12 functions as a transmission beam former and a reception beam former, obtains a voxel value for each voxel of a plurality of voxels forming a three-dimensional space, and outputs the voxel value to a noise removal processor 13.

The noise removal processor 13 judges a voxel as a noise voxel for a voxel having a significantly different voxel value with respect to the surrounding voxel values and executes a removal process. For example, the noise removal processor 13 calculates an average value of the voxel values corresponding to a total of 27 voxels, the target voxel and 26 voxels spatially adjacent to the target voxel, and sets the calculated average value as the voxel value of the target voxel. As a result, noise voxels which are spatially isolated can be removed. The voxel values of voxels to which the noise removal process is applied are stored in a first three-dimensional data memory 14.

In the first three-dimensional data memory 14, each voxel value is stored at an address corresponding to the coordinates within the three-dimensional space. In other words, the voxel values are stored at addresses corresponding to the coordinate values in an xyz orthogonal coordinate system. The coordinate system used in the first three-dimensional data memory 14 may alternatively be, for example, an rθφ polar coordinate system which is well suited for a sector scanning method of an ultrasonic beam.

A binarization processor 16 obtains the voxel value of each voxel from the first three-dimensional data memory 14 and, based on a threshold (threshold value) set for the voxel value, separates the voxels into a group of voxels having a voxel value greater than or equal to the threshold and a group of voxels having a voxel value less than the threshold. The "voxel value" refers to an echo level or Doppler information corresponding to the voxel. In the present embodiment, the echo level is considered as the voxel value. In general, an intracardial section of a heart has a smaller echo level than a cardiac muscle. Taking into this consideration, by setting the threshold at a level which is lower than a level corresponding to the cardinal muscle and higher than a level corresponding to the intracardial section, it is possible to separate the cardinal muscle and the intracardial section based on the threshold. For example, when the echo level value is of 64 gradations, a level for separating the cardinal muscle and the intracardial section appears around levels 7-9. In the present embodiment, the voxel value is an echo value of 64 gradations and the threshold is set at 8. An inverted binarization process is applied in which a voxel value of a voxel originally having a voxel value of 8 or greater (cardinal muscle voxel corresponding to the cardinal muscle) is set to 0 and a voxel value of a voxel originally having a voxel value of less than 8 (intracardial section voxel corresponding to the intracardial section) is set to 1. The voxel values of the voxels to which the inverted binarization process is applied in the binarization processor 16 are stored in a second three-dimensional data memory 18.

A labeling section 20 reads voxel values of voxels to which the inverted binarization process is applied from the second data memory 18 and applies a labeling process. Specifically, the labeling section 20 extracts a plurality of isolated groups of intracardial section voxels (voxels each having a voxel value of 1) from the group of voxel values to which the inverted binarization process is applied and attaches a number to each of the isolated groups. A heart has four cavities respectively corresponding to a left ventricle, a left atrium, a right ventricle, and a right atrium. Thus, each of the extracted isolated groups corresponds to each of the four cavities.

Figure 2:
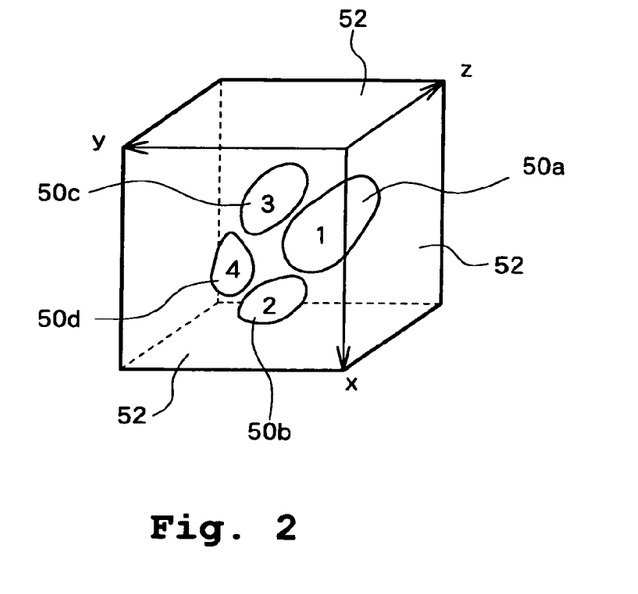
FIG. 2 is a diagram illustrating volume data to which a labeling process is applied.

FIG. 2 is a diagram illustrating a group (volume data) of voxel values to which the labeling process is applied in the labeling section 20. The voxels are separated into cardinal muscle voxels and intracardial section voxels by the inverted binarization process. In FIG. 2, the cavities 50a-50d correspond to the isolated groups of intracardial voxels. Further, the portion 52 other than the cavities 50a-50d correspond to a group of cardinal muscle voxels. The cavities 50a-50d correspond respectively to the left ventricle, left atrium, right ventricle, and right atrium. The isolated groups are labeled with numbers 1-4 by the labeling section 20.

Referring back to FIG. 1, a specific cavity extractor section 22 extracts an isolated group corresponding to the left ventricle from among the plurality of isolated groups to which numbers are attached in the labeling section 20. Because the cavity corresponding to the left ventricle has a larger volume than the other cavities, the specific cavity extractor section 22 extracts, from among the plurality of isolated groups, an isolated group having the maximum volume as the isolated group corresponding to the left ventricle (as a result of this, the cavity 50a assigned with a number of 1 in FIG. 2 is extracted). The volume of each isolated group is calculated from, for example, the number of voxels contained in the isolated group.

The specific cavity extractor section 22 extracts an isolated group corresponding to the left ventricle based on a designated coordinate designated by a user in the case of "auto OFF", that is, when an automatic extraction process is stopped by an automatic On/Off signal. The setting of the designated coordinate by the user is performed by the user designating a point within a left ventricle in a cross sectional image using a pointing apparatus such as a trackball while the user views a three-dimensional image or a cross sectional image of the heart displayed on a display section 44. When a designated coordinate is set at a point within the left ventricle, the specific cavity extractor section 22 extracts the isolated group containing the designated coordinate as the isolated group corresponding to the left ventricle. The designation by the user is not limited to the left ventricle, and, when extraction of other cavities such as the left atrium is desired, a designated coordinate may be set within the desired cavity and the specific cavity extractor section 22 may extract an isolated group corresponding to the desired cavity such as left atrium based on the designation by the user.

There may cases in which an isolated group extracted in the labeling section 20 does not correspond to any of the four cavities. For example, there may be a case in which cavities corresponding to the left ventricle and left atrium are extracted as one isolated group in which the corresponding cavities are connected. In this case, the user sets a region of interest in a cavity corresponding to the left ventricle and the specific cavity extractor section 22 extracts the isolated group within the set region of interest as the isolated group corresponding to the left ventricle. The voxel values of the voxels to which the extraction process for the left ventricle cavity is applied in the specific cavity extractor section 22 are stored in a third three-dimensional data memory 24.

A center-of-mass detector section 26 obtains the addresses of voxels to which the extraction process for the left ventricle cavity is applied from the third three-dimensional data memory 24 and determines a center of mass of the left ventricle cavity. Specifically, coordinates (Xo, Yo, Zo) of a volume center of mass of the left ventricle cavity in the xyz orthogonal coordinate system are calculated based on the three-dimensional coordinate values of all voxels corresponding to the left ventricle cavity. The calculated coordinates (Xo, Yo, Zo) of the center of mass is output to a major-axis end detector section 28.

The major-axis end detector section 28 finds an end of a major axis (major-axis endpoint) which is positioned furthest away from the center of mass among voxels corresponding to the left ventricle cavity based on the coordinates (Xo, Yo, Zo) of the center of mass of the left ventricle cavity calculated in the center-of-mass detector section 26 and addresses of voxels obtained from the third three-dimensional data memory 24. In other words, the major-axis end detector section 28 calculates, for each voxel corresponding to the left ventricle cavity, a distance between the three dimensional coordinates of the voxel and the coordinates of the center of mass (Xo, Yo, Zo), finds a voxel having the largest distance, and outputs the found voxel to a major-axis slope calculator section 30.

The major-axis slope calculator section 30 sets a straight line passing through the center of mass calculated in the center-of-mass detector section 26 and the major-axis end point found in the major-axis end detector section 28 as a major axis of the left ventricle. In addition, the major-axis slope calculator section 30 calculates a slope θ with respect to the x axis when the left ventricle major axis is projected onto the xy plane and a slope φ with respect to the x axis when the left ventricle major axis is projected onto the zx plane. The major-axis slope calculator section 30 outputs these slopes to a three-dimensional data rotator section 32.

Figure 3:
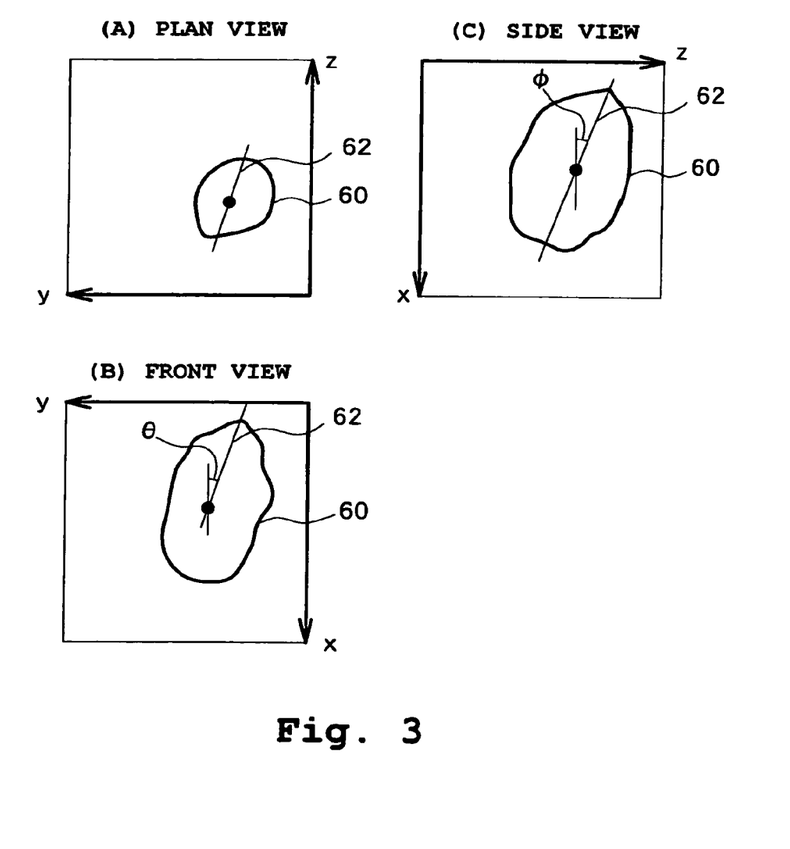
FIG. 3 is a diagram illustrating a slope calculated in a major-axis slope calculator section.

FIG. 3 is a diagram illustrating a slope calculated in the major-axis slope calculator section 30. FIGS. 3(A)-(C) respectively represent a plan view, a front view, and a side view of a left ventricle cavity 60. The front view shown in FIG. 3(B) is a view of the left ventricle cavity 60 projected onto the xy plane in the xyz orthogonal coordinate system. Thus, the slope of the left ventricle major axis 62 with respect to the x axis shown in the front view of FIG. 3(B) is θ. The side view shown in FIG. 3(C) is a view of the left ventricle cavity 60 projected onto the zx plane in the xyz orthogonal coordinate system. Thus, the slope of the left ventricle major axis 62 with respect to the x axis shown in the side view of FIG. 3(C) is φ.

Referring back to FIG. 1, the three-dimensional data rotator section 32 converts addresses of voxels in the second three-dimensional data memory 18 based on the center of mass calculated in the center-of-mass detector section 26 and slopes calculated in the major-axis slope calculator section 30 so that the left ventricle major axis becomes vertical with respect to the yz plane. In other words, with the coordinate of the center of mass (Xo, Yo, Zo) fixed, the three-dimensional data rotator section 32 converts the three-dimensional coordinate values of the voxels so that the left ventricle major axis is rotated on the xy plane by an angle of −θ and the left ventricle major axis is further rotated on the zx plane by an angle of −φ. The voxel values of the voxels are stored in a fourth three-dimensional data memory 34 with addresses attached which corresponds to the coordinate values (coordinate values of x'y'z' orthogonal coordinate system) of voxels obtained as a result of the conversion.

Figure 4:
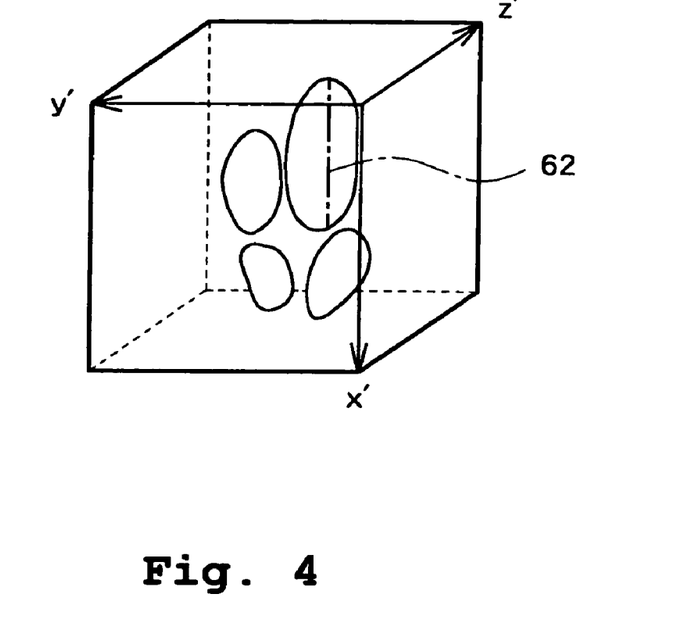
FIG. 4 is a diagram illustrating volume data to which a coordinate conversion process is applied by a three-dimensional data rotator section.

FIG. 4 is a diagram illustrating volume data to which the coordinate conversion process is applied in the three-dimensional data rotator section 32. FIG. 4 shows a result of the coordinate conversion process applied to the volume data shown in FIG. 2. In other words, FIG. 4 shows a result of conversion, in the three-dimensional data rotator section 32, of three-dimensional coordinate values of the voxels to the x'y'z' orthogonal coordinate system so that the left ventricle major axis 62 becomes vertical with respect to the yz plane. When the left ventricle major axis 62 becomes vertical to the yz plane, a calculation of a cross sectional area in subsequent steps can be simplified. It is also advantageous in the diagnosis process to display a cross sectional image with the left ventricle major axis 62 pointing in a particular direction.

Referring back to FIG. 1, a cavity cross sectional area calculator section 36 sets a cutting plane with respect to a heart and calculates a cavity cross sectional area which is an area of the cavity in the cutting plane based on the voxel values and addresses of voxels stored in the fourth three-dimensional data memory 34. The cutting plane is first set to a plane which is parallel to an x'y' plane in the x'y'z' orthogonal coordinate system and which includes the left ventricle major axis. When the cutting plane is set, a number of voxels on the cutting plane which has a voxel value of 1 (intracardial section voxel) is counted. The cavity cross sectional area calculator section 36 calculates the cross sectional area of the cavity based on the counted value. The group of voxels having a voxel value of 1 includes voxels corresponding to four cavities of the heart. In other words, the cross sectional area of cavity calculated in the cavity cross sectional area calculator section 36 corresponds to cross sectional areas regarding four cavities. The calculated cross sectional area of cavity is output to a comparator 38.

Figure 5:
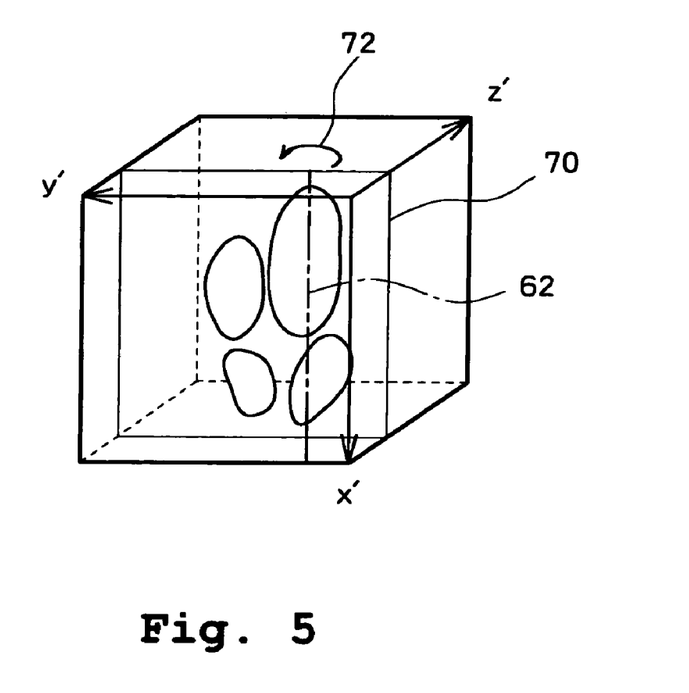
FIG. 5 is a diagram illustrating setting of a cutting plane in a cavity cross section calculator section.

FIG. 5 is a view illustrating setting of a cutting plane in the cavity cross sectional area calculator section 36. The cavity cross sectional area calculator section 36 calculates a cavity cross sectional area for each of a plurality of cutting planes including the left ventricle major axis 62. More specifically, with the cutting plane 70 which is originally set, that is, which is parallel to the x'y' plane and which contains left ventricle major axis 62, as an initial cutting plane, the cavity cross sectional area calculator section 36 calculates the cavity cross sectional area in the initial cutting plane, rotates the cutting plane 70 about the left ventricle major axis by a predetermined angle in a specified direction (rotational direction 72), calculates a cavity cross sectional area for each position of rotational angle until a rotational angle of 180° is reached, and outputs the calculated results to the comparator 38.

Referring back to FIG. 1, the comparator 38 and a maximum value latch section 40 extract a maximum area from among the cavity cross sectional areas for positions at different rotational angles calculated in the cavity cross sectional area calculator section 36 and find a rotational angle $\alpha_1$ of a cutting plane in which the maximum cavity cross sectional area can be obtained. More specifically, the comparator 38 compares the cavity cross sectional area in each position at a rotational angle sequentially output from the cavity cross sectional area calculator section 36 with a maximum cavity cross sectional area stored in the maximum value latch section 40. When the cavity cross sectional area output from the cavity cross sectional area calculator section 36 is larger than the maximum cavity cross sectional area stored in the maximum value latch section 40, the cavity cross sectional area stored in the maximum value latch section 40 is replaced by the cavity cross sectional area output from the cavity cross sectional area calculator section 36.

The comparator 38 compares each cavity cross sectional area for each rotational angle position from the initial cutting plane to a rotational angle of 180° with a cavity cross sectional area stored in the maximum value latch section 40. The maximum value latch section 40 outputs, to an optimum cross section setter 42, as $\alpha_1$, the rotational angle of the cutting plane ultimately stored in the maximum value latch section 40 as a result of comparisons of cavity cross sectional areas up to a rotational angle of 180°, the stored rotational angle corresponding to an angle in which the maximum cavity cross sectional area can be obtained. The detection of the rotational angle $\alpha_1$ is performed in the cavity cross sectional area calculator section 36, for example, with the predetermined angle being 1° and in units of 1° from the initial cutting plane until the rotational angle of 180°. Alternatively, it is also possible to find a maximum area in units of an angle of 15° from the initial cutting plane and then find a maximum area around the resulting rotational angle in units of 1°.

The optimum cross section setter 42 sets an optimum cross section based on the center of mass detected in the center-of-mass detector section 26, slopes calculated in the major-axis slope calculator section 30, and the rotational angle output from the maximum value latch section 40. The rotational angle $\alpha_1$ output from the maximum value latch section 40 defines a cutting plane in which the cross sectional area with respect to four cavities becomes the maximum. In other words, a cutting plane which is rotated, about the left ventricle major axis, by a rotational angle of $\alpha_1$ from a plane in the x'y'z' orthogonal coordinate system which is parallel to the x'y' plane and which contains the left ventricle major axis is defined as a cutting plane in which the cross sectional areas regarding four cavities are maximum. The optimum cross section setter 42 sets this cutting plane as a four-cavity cross section.

The optimum cross section setter 42 also sets a plane which is orthogonal to the set four-cavity cross section and which contains the left ventricle major axis as a two-cavity cross section. Moreover, the optimum cross section setter 42 sets a plane which is orthogonal to the left ventricle major axis and which contains the center of mass of the left ventricle as a minor-axis cross section. In this manner, the four-cavity cross section, two-cavity cross section, and minor-axis cross section are set in the x'y'z' orthogonal coordinate system.

The optimum cross section setter 42 sets cutting planes with respect to a plurality of voxel values stored in the first three-dimensional data memory 14, that is, for the group of three-dimensional image data. The voxel values stored in the first three-dimensional data memory 14 are stored, however, in addresses corresponding to the coordinate values in the xyz orthogonal coordinate system. In consideration of this, the optimum cross section setter 42 applies a coordinate conversion process identical to the coordinate conversion process applied in the three-dimensional data rotator section 32 to the voxel values stored in the first three-dimensional data memory 14. In other words, with the coordinate (Xo, Yo, Zo) of the center of mass found in the center-of-mass detector section 26 as a fixed point, the optimum cross section setter 42 converts the three-dimensional coordinate values of the voxels such that the left ventricle major axis is rotated by an angle of −θ on the xy plane and the left ventricle major axis is rotated by an angle of −ϕ on the zx plane. As a result, the coordinate values of voxels are converted into coordinate values of the x'y'z' orthogonal coordinate system.

The optimum cross section setter 42 sets the four-cavity cross section, two-cavity cross section, and minor-axis cross section for a group of three-dimensional image data in which the coordinate values are converted to the x'y'z' orthogonal coordinate system. The optimum cross section setter 42 creates a cross sectional image of the heart in each cross section and creates a stereographical image of the heart based on the group of three-dimensional image data. The optimum cross section setter 42 further forms a three-dimensional image in which plane images indicating the positions of the four-cavity cross section, two-cavity cross section, and minor-axis cross section are incorporated into the formed stereographical image of the heart. The three-dimensional image and cross sectional image in each cross section both of which are formed in the optimum cross section setter 42 are displayed on the display section 44.

Figure 6:
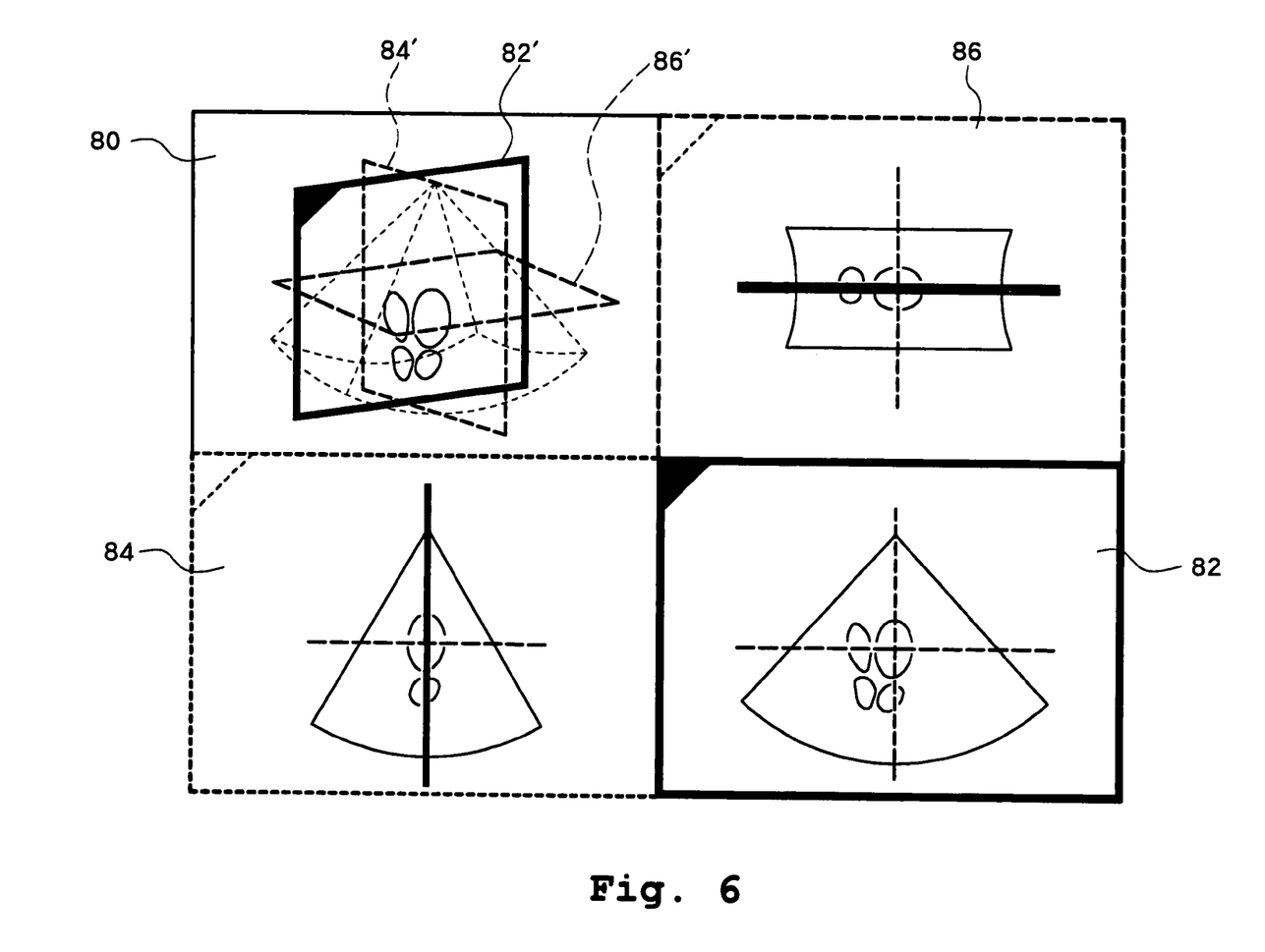
FIG. 6 is a diagram showing images displayed on a display section.

FIG. 6 is a diagram showing images displayed on the display section 44, and shows a three-dimensional image 80 including the four cavities of the heart, a four-cavity cross sectional image 82 at the four-cavity cross section, a two-cavity cross sectional image 84 at the two-cavity cross section, and a minor-axis cross sectional image 86 at the minor axis cross section. In the three-dimensional image 80, a cursor 82' for four-cavity cross section, a cursor 84' for two-cavity cross section, and a cursor 86' for minor-axis cross section are incorporated. Because each cursor is displayed in the position of the corresponding cross section, the user can identify the formation position of each cross sectional image based on the position of the cursor on the three-dimensional image 80. The user can change the positions of the cross sections as necessary while viewing the displayed image shown in FIG. 6.

As described, with an ultrasonic diagnostic apparatus shown in FIG. 1, a four-cavity cross section, a two-cavity cross section, and a minor-axis cross section a reset for a heart. The cross section which can be set by the ultrasonic diagnostic equipment of the present invention is not, however, limited to these cross sections. For example, in the cavity cross sectional area calculator section 36, it is possible to consider the cross sectional area of the left ventricle cavity alone and define a cutting plane in which the cross sectional area of the left ventricle cavity is maximized. Then, three orthogonal cross sections regarding the left ventricle can be set by setting two cross sections which are orthogonal to the cutting plane in the optimum cross section setter 42. In addition, the target tissue is not limited to the heart, and cross sections regarding other tissues may also be set.

In the ultrasonic diagnostic equipment shown in FIG. 1, a configuration is shown in which a maximum cross sectional area is found from among cavity cross sections at various rotational angles using a cavity cross sectional area calculator section 36, comparator 38, and a maximum value latch section 40. Alternatively, it is also possible to extract a cross section having the minimum cross sectional area from among the cavity cross sections at various rotational angles. Moreover, it is also possible to employ a configuration in which peripheral lengths of the cavity cross sections at various rotational angles are determined and a cross section is extracted in which the peripheral length is maximized or minimized.

A preferred embodiment of the present invention has been described. However, this embodiment is for exemplifying purpose only and should in no way be interpreted as limiting or restricting the scope of the present invention.

What is claimed is:

1. An ultrasonic diagnostic apparatus for obtaining volume data made of voxel values for voxels forming a three-dimensional space by transmitting and receiving ultrasound to and from the three-dimensional space containing a target tissue and for applying a data process with respect to the volume data, the ultrasonic diagnostic apparatus comprising:
- an isolated group extractor for extracting a plurality of isolated groups corresponding to the target tissues in the volume data;
- a specific isolated group extractor for extracting an isolated group having a maximum volume from among the plurality of isolated groups as a specific isolated group in the volume data;
- a basis axis setter for setting a basis axis in the specific isolated group based on a shape of the specific isolated group included in the plurality of isolated groups in the volume data;
- a reference cross section setter for setting a plurality of reference cross sections each having a different rotational angle from each other, with the basis axis as an axis of rotation, in the volume data;
- a basis cross section selector for selecting a basis cross section from among the plurality of reference cross sections based on a size of a cross sectional area of the target tissue in each of the reference cross sections set in the volume data;
- a cross sectional image former for forming a cross sectional image of the target tissue based on the volume data, the cross sectional image corresponding to one of the plurality of reference cross sections set with the basis cross section as a reference and the basis cross section; and
- a means for displaying said cross sectional image.

2. The ultrasonic diagnostic apparatus according to claim 1, wherein
the basis axis setter sets the basis axis based on two characteristic points of the specific isolated group.

3. The ultrasonic diagnostic apparatus according to claim 1, wherein
the basis axis setter sets the basis axis based on a center of mass of the specified isolated group and one characteristic point of the specified isolated group other than the center of mass.

4. The ultrasonic diagnostic apparatus according to claim 1, wherein
the basis axis setter sets the basis axis based on the center of mass of the specified isolated group and an end, in the specified isolated group, which is furthest away from the center of mass.

5. The ultrasonic diagnostic apparatus according to claim 1, wherein
the reference cross section setter sequentially rotates a specific plane containing the basis axis by a predetermined angle with the basis axis as an axis of rotation to set the planes formed in each rotational angle position as the plurality of reference cross sections.

6. The ultrasonic diagnostic apparatus according to claim 1, wherein
the basis cross section selector calculates an area of a cross section of the target tissue in each reference cross section and selects, as the basis cross section, a reference cross section having a maximum cross sectional area.

7. The ultrasonic diagnostic apparatus according to claim 1, wherein
the basis cross section selector calculates a cross sectional area of the target tissue in each reference cross section and selects, as the basis cross section, a reference cross section in which a minimum cross sectional area can be obtained.

8. An ultrasonic diagnostic apparatus for obtaining volume data made of voxel values for voxels forming a transmission space by transmitting and receiving ultrasound to or from a heart having four cavities including a left ventricle cavity and for applying a data process to the volume data, the ultrasonic diagnostic apparatus comprising:
- a major axis setter for setting a left ventricle major axis based on the shape of the left ventricle cavity selected from the four cavities such that the left ventricle major axis passes a center of mass of the left ventricle cavity, in the volume data;
- a reference cross section setter for setting a plurality of reference cross sections each having a different rotational angle from each other in the volume data, with the left ventricle major axis as an axis of rotation;
- a basis cross section selector for selecting a basis cross section from among the plurality of reference cross sections based on a size of a cross section of the four cavities in each of the reference cross sections set in the volume data;
- a cross sectional image former for forming a cross sectional image corresponding to each of a four-cavity cross section, a two-cavity cross section, and a minor-axis cross section, all of which relate to the heart, based on the volume data and the basis cross section; and
- a means for displaying said cross sectional image, wherein
the basis cross section selector calculates a cross sectional area of the four cavities in each of the reference cross sections and selects, as the basis cross section, a reference cross section in which a maximum cross sectional area can be obtained, and
the cross sectional image former sets the basis cross section as the four-cavity cross section, sets a cross section which is orthogonal to the basis cross section and includes the left ventricle major axis as the two-cavity cross section, and sets a cross section which is orthogonal to the left ventricle major axis and includes the center of mass of the left ventricle cavity as the minor axis cross section.

9. The ultrasonic diagnostic apparatus according to claim 8, further comprising:
- a binarization section for separating the voxels into cavity tissue voxels and real tissue voxels to create binarized volume data;
- a cavity group extractor for extracting a plurality of cavity groups each made of a plurality of cavity tissue voxels based on the binarized volume data; and
- a left ventricle cavity selector for selecting a left ventricle cavity group corresponding to the left ventricle cavity from among the plurality of cavity groups, wherein
the major axis setter judges the shape of the left ventricle cavity based on the left ventricle cavity group.

10. The ultrasonic diagnostic apparatus according to claim 8, further comprising:
- a three-dimensional image former for forming a three-dimensional image in which at least one cursor indicating at least one of the positions of the four-cavity cross section, the two-cavity cross section, and the minor-axis cross section is displayed on a stereographical image of the heart obtained based on the volume data.

* * * * *